United States Patent
Ali et al.

(10) Patent No.: US 12,202,846 B1
(45) Date of Patent: Jan. 21, 2025

(54) FEAZD, NIAZD, AND CUAZD COMPLEXES INCORPORATING 1-(2-HYDROXYPHENYLAZO)-2-NAPHTHOL ($H_2$AZD) FOR BIOLOGICAL APPLICATIONS

(71) Applicant: KING FAISAL UNIVERSITY, Al-Ahsa (SA)

(72) Inventors: Mai Mostafa Khalaf Ali, Al-Ahsa (SA); Hany Mohamed Abd El-Lateef Ahmed, Al-Ahsa (SA); Antar Ahmed Abdelhamid Ahmed, Al-Ahsa (SA); Aly Abdou, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/417,945

(22) Filed: Jan. 19, 2024

Related U.S. Application Data (62) Division of application No. 18/233,210, filed on Aug. 11, 2023.

(51) Int. Cl.
| | |
|---|---|
| *C07F 15/02* | (2006.01) |
| *A61P 31/04* | (2006.01) |
| *A61P 31/10* | (2006.01) |
| *C07F 1/08* | (2006.01) |
| *C07F 15/04* | (2006.01) |

(52) U.S. Cl.
CPC ............ *C07F 15/025* (2013.01); *A61P 31/04* (2018.01); *A61P 31/10* (2018.01); *C07F 1/08* (2013.01); *C07F 15/045* (2013.01); *C07B 2200/13* (2013.01)

(58) Field of Classification Search
CPC ........ C07F 15/025; C07F 1/08; C07F 15/045; A61P 31/04; A61P 31/10; C07B 2200/13
See application file for complete search history.

(56) References Cited

PUBLICATIONS

Abd El-Lateef et al. ACS Omega. 2023; 8: 25877-25891. (Year: 2023).*
Mohammed. The Scientific World Journal. Article ID 9943763, 9 pages. (Year: 2021).*
NPL-1: Lima et al., "Synthesis, Structure and Biological Evaluation of Mixed Ligand Oxidovanadium(IV) Complexes Incorporating 2-(Arylazo)Phenolates", New Journal of Chemistry, Issue 45, 2019.
NPL-2: Murata et al., "The Role of Coulomb Interactions for Spin Crossover Behaviors and Crystal Structural Transformation in Novel Anionic Fe(III) Complexes From a Π-Extended ONO Ligand", Crystals 2016, 6(5), 49.
NPL-3: Seok et al., "Synthesis of New Metal Complex Derivatives Based on AZO, Naphthol and Pyrazole Moieties for Color Filter Pigments", Molecular Crystals and Liquid Crystals, vol. 529, 2010—Issue 1.

* cited by examiner

*Primary Examiner* — David Browe
(74) *Attorney, Agent, or Firm* — Nath, Goldberg & Meyer; Joshua B. Goldberg

(57) ABSTRACT

A method of treating a microbial infection in a patient is provided, including steps of administering to a patient in need thereof a therapeutically effective amount of a metal-1-(2-hydroxyphenylazo)-2-naphthol ($H_2$AZD) complex, wherein the metal is Fe(III), Ni(II), or Cu(II) and the metal is complexed with a 1-(2-hydroxyphenylazo)-2-naphthol ($H_2$AZD) ligand.

3 Claims, 5 Drawing Sheets

FEAZD, NIAZD, AND CUAZD COMPLEXES INCORPORATING 1-(2-HYDROXYPHENYLAZO)-2-NAPHTHOL (H₂AZD) FOR BIOLOGICAL APPLICATIONS

CROSS-REFERENCE TO RELATED APPLICATION

This application is a divisional of U.S. patent application Ser. No. 18/233,210, filed on Aug. 11, 2023, the entire contents of which are incorporated herein by reference.

BACKGROUND

1. Field

The present disclosure relates to three new Fe(III) (FeAZD), Ni(II) (NiAZD), and Cu(II) (CuAZD) complexes incorporating 1-(2-hydroxyphenylazo)-2-naphthol ($H_2AZD$), their synthesis, and their use for antibacterial and antifungal applications.

2. Description of the Related Art

Over recent decades, various metal complexes have been studied for their potential antimicrobial effects. The design and development of such new biomaterials and molecular frameworks have increased rapidly, addressing the coordination chemistry of biologically active chelates.

Certain such efforts have focused on complexes involving various azo-dye-based ligands, including complexes incorporating the 1-(2-hydroxyphenylazo)-2-naphthol ($H_2AZD$) ligand. The formation of complexes between $H_2AZD$ and various metals have been studied. However, to date, not metal-$H_2AZD$ metal complexes have been obtained having the right combination of antimicrobial effectiveness, ease and desirable cost of manufacture, and which involve green synthesis processes.

Thus, new metal-$H_2AZD$ complexes solving the aforementioned problems are desired.

SUMMARY

The present subject matter relates to three new Fe(III) (FeAZD), Ni(II) (NiAZD), and Cu(II) (CuAZD) complexes incorporating 1-(2-hydroxyphenylazo)-2-naphthol ($H_2AZD$), their synthesis, and their use for antibacterial and antifungal applications.

In an embodiment, the present subject matter relates to a metal-1-(2-hydroxyphenylazo)-2-naphthol ($H_2AZD$) complex, wherein the metal is Fe(III), Ni(II), or Cu(II) which is complexed with a 1-(2-hydroxyphenylazo)-2-naphthol ($H_2AZD$) ligand, and the complex is selected from the group consisting of:

FeAZD complex;

NiAZD complex; and

CuAZD complex.

In another embodiment, the present subject matter relates to a pharmaceutically acceptable composition comprising a therapeutically effective amount of the metal-1-(2-hydroxyphenylazo)-2-naphthol ($H_2AZD$) complex as described herein and a pharmaceutically acceptable carrier.

In an embodiment, the present subject matter relates to a method of treating a microbial infection in a patient, comprising administering to a patient in need thereof a therapeutically effective amount of the metal-1-(2-hydroxyphenylazo)-2-naphthol ($H_2AZD$) complex as described herein.

In a further embodiment, the present subject matter relates to a method of making the metal-1-(2-hydroxyphenylazo)-2-naphthol ($H_2AZD$) complex as described herein, the method comprising: adding a solution of a salt of the metal in water to ethanol containing the 1-(2-hydroxyphenylazo)-2-naphthol ($H_2AZD$) ligand while heating to obtain a mixture; heating the mixture with constant stirring for at least about 15 hours; filtering the mixture to obtain a yielded compound; and drying, washing, and recrystallizing the yielded compound to obtain the metal-1-(2-hydroxyphenylazo)-2-naphthol ($H_2AZD$) complex.

These and other features of the present subject matter will become readily apparent upon further review of the following specification.

BRIEF DESCRIPTION OF THE DRAWINGS

FIGS. 1A-1F show mass spectra plots of the FeAZD (1A), NiAZD (1B), and CuAZD (1C) complexes, while FIGS. 1D-1F show T.G./D.T.G. curves of the FeAZD (1D), NiAZD (1E), and CuAZD (1F) complexes.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a metal-1-(2-hydroxyphenylazo)-2-naphthol ($H_2AZD$) complex, wherein the metal is Fe(III), Ni(II), or Cu(II) which is complexed with a 1-(2-hydroxyphenylazo)-2-naphthol ($H_2AZD$) ligand, and the complex is selected from the group consisting of:

FeAZD complex;

NiAZD complex; and

CuAZD complex.

In this regard, these three new Fe(III) (FeAZD), Ni(II) (NiAZD), and Cu(II) (CuAZD) complexes can be synthesized and characterized using various physicochemical and spectroscopic approaches. The $H_2AZD$ ligand can act as a bi-basic, bi-dentate NO ligand in a 1:1 molar ratio with the specific metal being used.

In this regard, in an embodiment, the metal and the 1-(2-hydroxyphenylazo)-2-naphthol ($H_2AZD$) ligand can be present in the complex in a 1:1 molar ratio.

In another embodiment, the FeAZD complex and the CuAZD complex each can have an octahedral geometry. Similarly, the NiAZD complex can have a tetrahedral geometry.

In certain embodiments, the optimized geometry, HOMO, and LUMO analysis of the ligand and its metal complexes can be determined via Density functional theory (DFT) using the B3LYP with 6-311G(d,p), and LanL2DZ level of theory. In this regard, as described herein, the FeAZD complex can have an energy g of about 7.40 eV, the NiAZD complex can have an energy g of about 7.93 eV, and the CuAZD complex can have an energy go of about 7.06 eV. Each of these energies can be lower than that of the free ligand (9.58 eV). Further, since it has the lowest energy, in an embodiment the CuAZD is the most active of the currently described complexes.

In another embodiment, the present subject matter relates to a pharmaceutically acceptable composition comprising a therapeutically effective amount of the metal-1-(2-hydroxyphenylazo)-2-naphthol ($H_2AZD$) complex as described herein and a pharmaceutically acceptable carrier.

In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for a microbial infection. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of a microbial infection, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for foods or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of diseases such as microbial infections.

Accordingly, in a further embodiment, the present subject matter relates to a method of treating a microbial infection in a patient, comprising administering to a patient in need thereof a therapeutically effective amount of the metal-1-(2-hydroxyphenylazo)-2-naphthol ($H_2AZD$) complex as described herein.

In certain embodiments, the microbial infection treatable herein can be a bacterial infection or a fungal infection. In this regard, the bacterial infection or the fungal infection can be caused by one or more of *E. coli, P. aeruginosa, S. aureus, B. cereus, T. rubrum, C. albicans,* and *A. flavus.*

In certain embodiments, the metal complexes as described herein can have higher antibacterial and antifungal activity than the corresponding free ligand, $H_2AZD$.

In certain embodiments, any of the FeAZD, NiAZD, and/or CuAZD as described herein can be used for treating a microbial infection.

In one embodiment, the present subject relates to a method of treating a microbial infection in a patient, comprising administering to a patient in need thereof a therapeutically effective amount of the CuAZD complex as described herein. In this regard, the CuAZD complex can have good antibacterial and/or antifungal activity against *E. coli, P. aeruginosa, S. aureus, B. cereus, A. flavus, T. rubrum,* and *C. albicans.* In certain embodiments, the use of the CuAZD complex can exhibit activity indexes of 72.22%, 65.01%, 77.78%, 72.22%, 63.16%, 59.09%, and 61.90% against the noted bacteria and/or fungi, respectively. Similar results are expected for the FeAZD and NiAZD complexes described herein.

In another embodiment, the present metal complexes can show a lower MIC (6.25-3.125 ppm) compared to the free ligand (about 50 ppm).

In a further embodiment, the present metal complexes can inhibit the growth of *E. coli* (PDB ID: 5iq9). In this regard, such activity can be a result of binding affinity of the metal complexes to the relevant *E. coli* receptor. In an embodiment, the CuAZD can have the highest binding affinity to the receptor, with a more negative docking score of about −7.05 Kcal/mol, and lower inhibition constant (Ki) of about 6.90 µM.

The present subject matter further relates to a method of treating or preventing a disease comprising administering to a patient in need thereof a therapeutically effective amount of the complex herein.

In particular, the present subject matter relates to a method of treating one of the above-mentioned diseases or disorders comprising administering to a patient in need thereof a therapeutically effective amount of the complex herein.

In the above methods, the patient is preferably a mammal, more preferably a human. In an embodiment, the present complex can be used in combination therapy with one or more additional active agents.

In a further embodiment, the present subject matter relates to a method of making the metal-1-(2-hydroxyphenylazo)-2-naphthol ($H_2AZD$) complex as described herein, the method comprising: adding a solution of a salt of the metal in water to ethanol containing the 1-(2-hydroxyphenylazo)-2-naphthol ($H_2AZD$) ligand while heating to obtain a mixture; heating the mixture with constant stirring for at least about 15 hours; filtering the mixture to obtain a yielded compound; and drying, washing, and recrystallizing the yielded compound to obtain the metal-1-(2-hydroxyphenylazo)-2-naphthol ($H_2AZD$) complex. This synthesis method can be further understood by referring to the following Scheme 1:

In an embodiment of the present production methods, the salt of the metal used can be $FeCl_2$, $NiCl_2$, or $CuCl_2$.

In a further embodiment, the first mixture can be sonicated for at least about 60 minutes.

In another embodiment of the present production methods, the heating step can be conducted at a temperature of about 80° C. to about 90° C., about 80° C., about 81° C., about 82° C., about 83° C., about 84° C., about 85° C., about 86° C., about 87° C., about 88° C., about 89° C., about 90° C., or about 85° C.

In a further embodiment of the present production methods, the washing of the yielded compound can be with $H_2O$—$CH_3CH_2OH$.

In one embodiment, the metal-1-(2-hydroxyphenylazo)-2-naphthol ($H_2AZD$) complex is FeAZD which is obtained as a dark violet crystalline powder. In another embodiment, the metal-1-(2-hydroxyphenylazo)-2-naphthol ($H_2AZD$) complex is NiAZD which is obtained as an orange-red crystalline powder. In a further embodiment, the metal-1-(2-hydroxyphenylazo)-2-naphthol ($H_2AZD$) complex is CuAZD which is obtained as a pale green crystalline powder.

In certain embodiments of the present production methods, the salt of the metal and the 1-(2-hydroxyphenylazo)-2-naphthol ($H_2AZD$) ligand can be added in an about 1:1 molar ratio.

In a further embodiment, the present production methods can result in a yield of the metal-1-(2-hydroxyphenylazo)-2-naphthol ($H_2AZD$) complex of at least about 90%, at least about 91%, at least about 92%, at least about 93%, at least about 94%, at least about 95%, or at least about 90%. In an embodiment, the FeAZD can be prepared having a yield of at least about 93%. Similarly, the NiAZD can be prepared Scheme 1 having a yield of at least about 90%. Likewise, the CuAZD can be prepared having a yield of at least about 95%

The following examples relate to various methods of manufacturing certain specific complexes as described herein. All compound numbers expressed herein are with reference to the synthetic pathway FIGURES shown above.

EXAMPLES

Example 1

Preparation of the 1-(2-hydroxyphenylazo)-2-naphthol ligand ($H_2AZD$)

A first step relates to the preparation of a diazonium compound of the 2-aminophenolas azo compound. In a 100-ml round-bottom flask with a magnetic stirring bar, 1.09 grams of 2-aminophenol (0.01 mol) and 0.036 liter of HCl were mixed together. Then, 0.69 grams of $NaNO_2$ (10 ml mol) dissolved in 30 cm$^3$ of $H_2O$, was slowly added. Through the addition, the solution temperature was kept under 278 K. The resulting diazonium compound solution was stored in an airtight flask in the freezer at all periods. When investigated with iodine-starch test paper, the diazonium compound produces a blue-black dye. The diazonium salt coupling process should be initiated as soon as conditions allow.

The second step relates to a coupling procedure. A solution of sodium hydroxide (20% w/v) was supplemented to 1.44 g of B-naphthol (0.01 mol) in a 100 mL round-bottom flask. Once the temperature reached 0-5 degrees Celsius, the flask was removed from the ice bath. After being stirred for 45 minutes, the frozen diazonium compound was added slowly. The final azo product was obtained by filtering the crude product, washing it thoroughly in icy $H_2O$, and recrystallizing it in an appropriate solvent.

In the $H_2AZD$ IR analysis, a broad-OH absorption band was observed between 3127-3231 cm$^{-1}$ and C—H arom band at 3013 cm$^{-1}$. The N═N group's unique bands in stretching vibration absorption were also detected at 1558 cm$^{-1}$. $^1$H-NMR spectra of $H_2AZD$ showed a singlet signal for the —OH group at 9.93 ppm and aromatic signals at 7.76-7.14 ppm. The $^{13}$CNMR spectra showed signals at the following frequencies: 155.65, 145.23, 135.03, 129.80, 128.19, 128.00, 126.63, 126.42, 123.16, 119.04, and 109.12.

Dark reddish compound; Yield (92%); mp. 233-235° C.; IR (cm$^{-1}$): 3127-3231 (OH), 3013 (CH-aromatic); $^1$H NMR (400 MHZ, DMSO-$d_6$) δ (ppm): 9.93 (s, 1H, OH), 7.76-7.14 (m, 11H, (10 Ar—H+OH)); $^{13}$C NMR (100 MHz, DMSO-$d_6$) δ (ppm): 155.65, 145.23, 135.03, 129.80, 128.19, 128.00, 126.63, 126.42, 123.16, 119.04, 109.12; Elemental analysis for $C_{16}H_{12}N_2O_2$ (Calcd./Found); C, 72.72/72.54; H, 4.55/4.49; N, 10.60/10.55.

Example 2

Metal Complex Preparation

A solution of the metal salt (1.50 ml mol) in $H_2O$ (30 mL) was added slowly to ethanol containing the ligand (1.50 mmol) while heating the mixture. The mixture was heated for 15 hours in a water bath kept at 85° C. with constant stirring. After the yielded compound was filtered, dried, and washed with $H_2O$—$CH_3CH_2OH$ (1:2), it was recrystallized. The yield and melting/decomposition temperatures for each produced compound was determined, as per Scheme 1, above.

The metal complex compounds that were formed are able to remain stable at 25° C. and are not soluble in $H_2O$ but can be dissolved in DMF and acetonitrile. Table 1 below demonstrates the molar conductivity and elemental analysis of the created complexes. Theoretical and experimental elemental analyses of the metal complex compounds match up relatively well. The low molar conductivity values for FeAZD (8.79 $Ω^{-1}cm^2mol^{-1}$), NiAZD (8.27 $Ω^{-1}cm^2mol^{-1}$), and CuAZD (9.44 $Ω^{-1}cm^2mol^{-1}$) demonstrate the metal complexes do not have an electrolytic nature.

Infrared spectra was collected to gain a better appreciation of the relationship between the $H_2AZD$ ligand and metal ion. Table 1, below, demonstrates the most significant infrared bands that can be used to determine the best combination of ligand and metal. These bands are likely caused by the interaction between the coordinating centers of the ligand and the metal ion.

The azo (—N═N—) band was found in the free ligand's infrared spectra at 1558 cm$^{-1}$.

This band was also present in the $H_2AZD$ ligand's infrared spectra after coordination with the metal ion, but at an inferior wave number, 1482-1490 cm$^{-1}$, Table 1, below, indicating coordination with the azo-nitrogen.

The phenolic hydroxyl (—OH) band was detected between 3127 and 3231 cm$^{-1}$. The phenolic (—OH) vibration also disappeared in the metal complex compounds, proposing that the phenolic oxygen of the ligand plays a role in the formation of the C—O—M bond during deprotonation. This data shows that the complexes have two new spectral bands at 475-490 and 588-597 for v(M-N) and v(M-O), respectively.

Overall, this data suggests that the azo-ligand ($H_2AZD$) functions as a bi-negatively bi-dentate ligand, forming complex compounds through both its azo-nitrogen (—N═N—) and hydroxyl of phenol.

TABLE 1

Physical properties, conductivity, Uv-vis, magnetic, and FT-IR results.

| | | $H_2AZD$ | FeAZD | NiAZD | CuAZD |
|---|---|---|---|---|---|
| Physical properties | Color | Dark red | Dark violet | Orange-red | Pale green |
| | Melting point (° C.) | 233-235 | 280-283 | 275-277 | 265-267 |
| | Yield (%) | 92 | 93 | 90 | 95 |
| conductivity | $μ_v$, $Ω^{-1}cm^2mol^{-1}$ | — | 8.79 | 8.27 | 9.44 |
| | assignment | — | | Non-electrolyte | |
| UV-vis. | $λ_{max}$, nm | 385 | 495 | 515 | 630 |
| | assignment | π – π* | $^6A_{1g} \to {}^4T_{2g}(G)$ | $^3T_1 \to {}^3T_1$ (P) | $^2B_{1g} \to {}^2A_{1g}$ |
| Magnetic | $μ_{eff}$ (B.M) | — | 5.87 | 2.91 | 1.71 |
| | assignment | — | $d^5$ ($t_{2g}^3$ $e_g^2$) octahedral | $d^8$ ($e^4$ $t_2^4$) tetrahedral | $d^9$ ($t_{2g}^6$ $e_g^3$) octahedral |
| Stoichiometry | M : L | — | 1:1 | 1:1 | 1:1 |

TABLE 1-continued

Physical properties, conductivity, Uv-vis, magnetic, and FT-IR results.

|  |  | H$_2$AZD | FeAZD | NiAZD | CuAZD |
|---|---|---|---|---|---|
| IR spectra | υ (—OH) | 3127-3231 | 3475 | 3488 | 3480 |
|  | υ (—N=N) | 1558 | 1482 | 1490 | 1485 |
|  | υ (M—O) | — | 590 | 588 | 597 |
|  | υ (M—N) | — | 475 | 485 | 490 |
| EA | C | 72.72 (72.54) | 49.58 (49.33) | 56.67 (56.69) | 50.04 (50.59) |
| Found (calc.) % | H | 4.55 (4.49) | 3.22 (3.62) | 3.19 (3.57) | 4.38 (4.25) |
|  | N | 10.60 (10.55) | 7.18 (7.19) | 8.77 (8.26) | 7.99 (7.37) |
|  | M | — | 14.87 (14.33) | 17.41 (17.32) | 16.58 (16.73) |

Figure 1A:
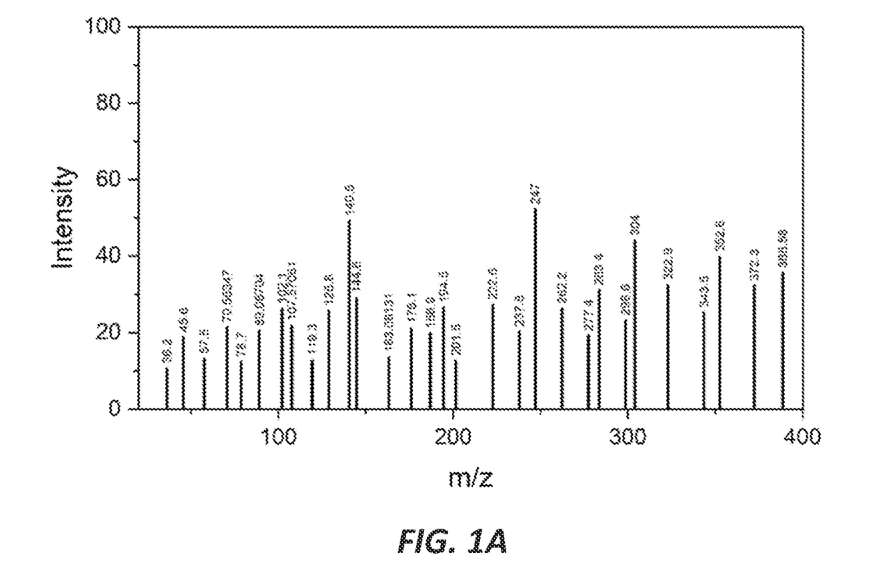
Figure 1B:
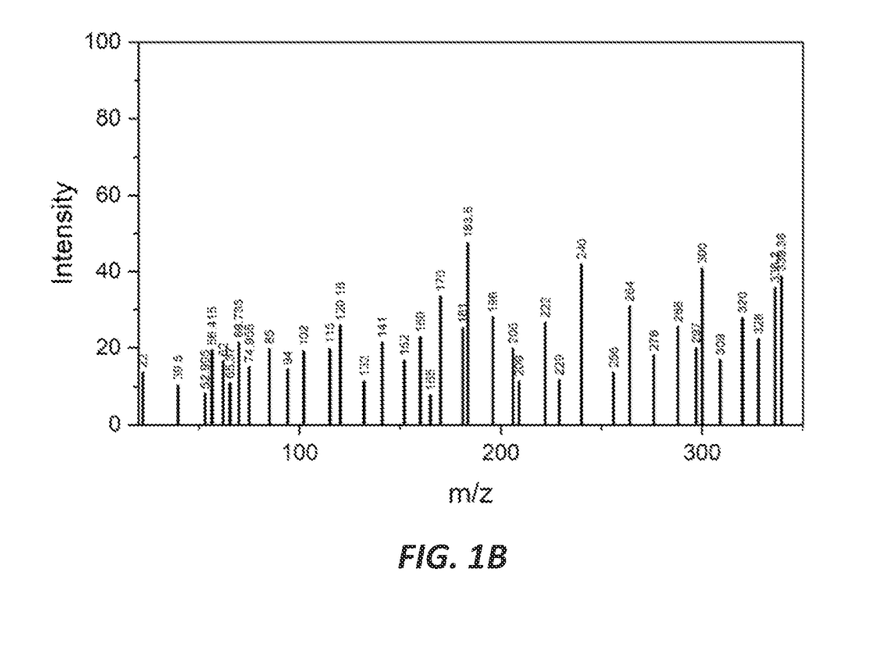
Figure 1C:
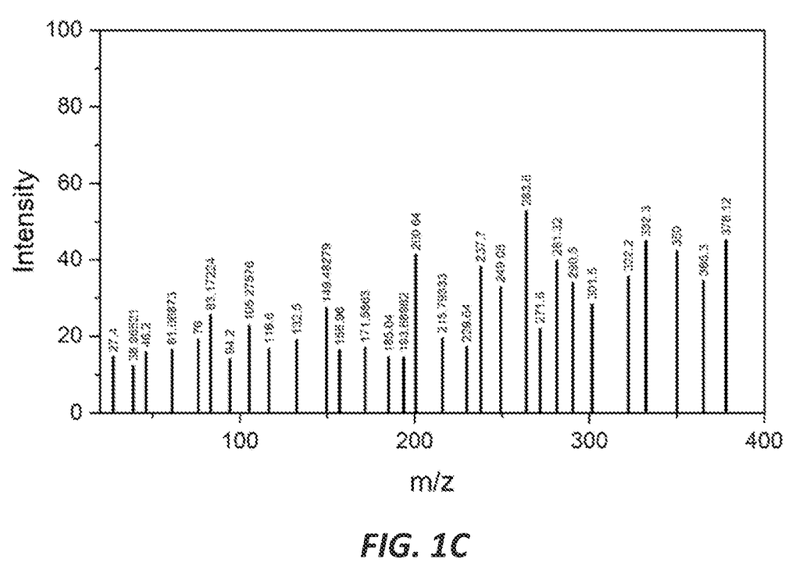
Figure 1D:
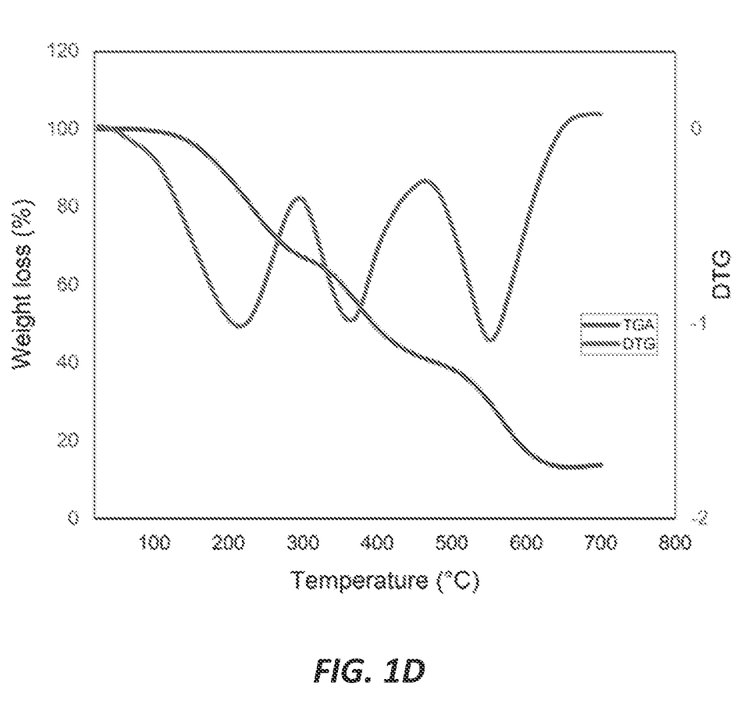
Figure 1E:
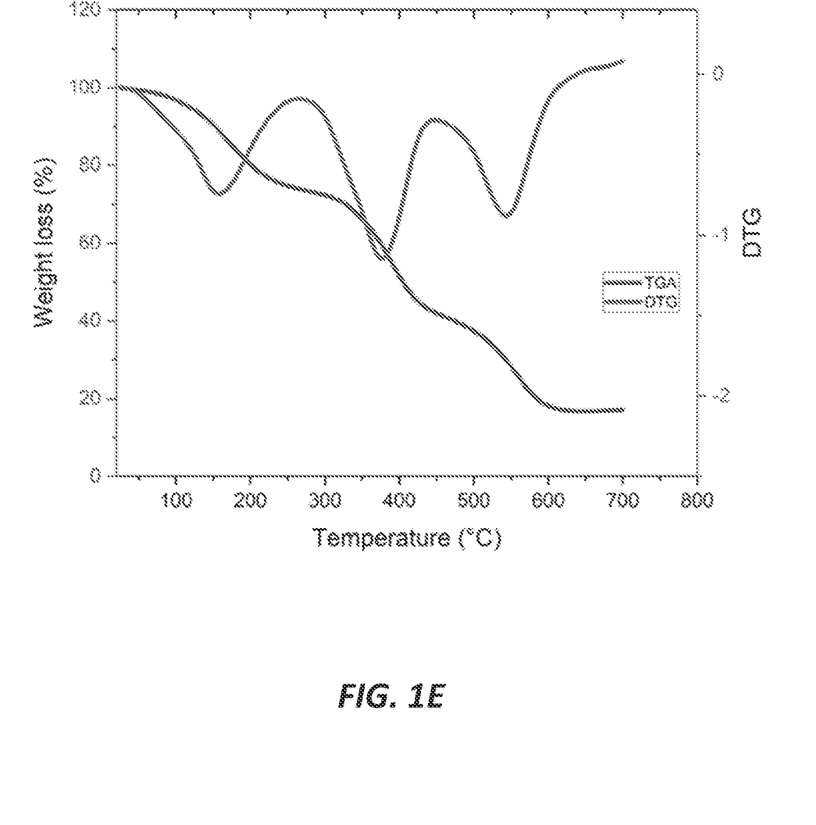
Figure 1F:
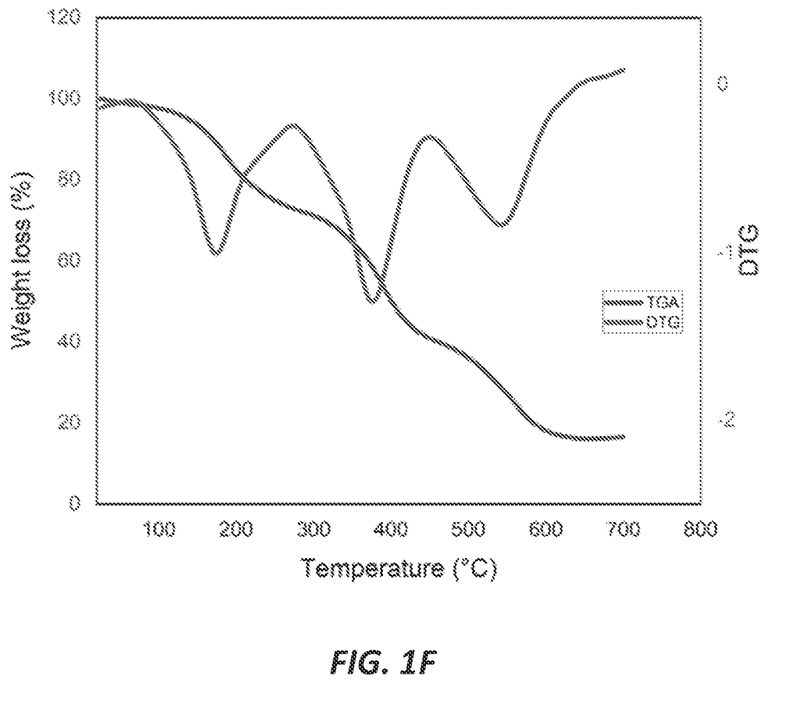

Mass spectra (MS) are used to analyze relative amounts between elements in a compound by examining their patterns. In the present study, the mass spectra of the metal complex compounds was studied, as shown in FIGS. 1A-1F. The molecular ion peak (M$^+$) in the mass spectra of the FeAZD, NiAZD, and CuAZD complexes (388.58, 339.36, and 378.12) are a good match with the expected values (389.59, 338.97, and 379.85). Other peaks in the mass spectra may be due to the unique characteristics of the metal complex compounds. The mass spectra analysis is consistent with the known values for C, H, and N, as well as the proposed structure.

Example 3

In Vitro Investigation of Bioactivity

The in vitro antibacterial and antifungal activity of the components was assessed using a series of bacteria (Pseudomonas aeruginosa (−ve), Staphylococcus aureus (+ve), Escherichia coli (−ve), and Bacillus cereus (+ve)) and fungi (Trichophyton rubrum, Aspergillus flavus, and Candida albicans). The disc diffusion method was used to perform the in vitro antimicrobial activity tests. The biological activity of each compound was determined by examining its impact on the size of the inhibition zone, which is a measure of the compound's effectiveness in inhibiting the growth of microorganisms. The inhibitory zone (IZ) surrounding the disc was measured in millimeters. The activity of the current compounds was compared to that of the standard antibiotic chloramphenicol, and the % Activity Index (%=IZ of test compound/IZ of Standard)×100, was evaluated. The results, presented in Table 2 below, indicate that the metal complex compound had a higher inhibition zone and a lesser minimum inhibitory dose (MIC) compared to the free ligand.

TABLE 2

The Anti-bacterial and Anti-fungal activity of the titled components in terms of inhibition zone (IZ, mm), and activity index (%)

Anti-bacterial activity

| bacterial strains |  | H$_2$AZD | FeAZD | NiAZD | CuAZD |
|---|---|---|---|---|---|
| Pseudomonas aeruginosa | IZ | 8 | 11 | 11 | 13 |
|  | % | 44.44 | 61.11 | 61.11 | 72.22 |
|  | MIC | 50 | 12.5 | 12.5 | 6.25 |
| Escherichia coli (−ve) | IZ | 8 | 12 | 11 | 13 |
|  | % | 40.00 | 60.00 | 55.00 | 65.00 |
|  | MIC | 50 | 6.25 | 6.25 | 3.125 |
| Staphylococcus aureus (+ve) | IZ | 9 | 13 | 13 | 14 |
|  | % | 50.00 | 72.22 | 72.22 | 77.78 |
|  | MIC | 50 | 6.25 | 6.25 | 6.25 |
| Bacillus cereus (+ve) | IZ | 8 | 12 | 11 | 13 |
|  | % | 44.44 | 66.67 | 61.11 | 72.22 |

TABLE 2-continued

The Anti-bacterial and Anti-fungal activity of the titled components in terms of inhibition zone (IZ, mm), and activity index (%)

|  | MIC | 50 | 6.25 | 6.25 | 6.25 |
|---|---|---|---|---|---|

Anti-fungal activity

| fungal strains |  | H$_2$AZD | FeAZD | NiAZD | CuAZD |
|---|---|---|---|---|---|
| Aspergillus flavus | IZ | 8 | 10 | 10 | 12 |
|  | % | 42.11 | 52.63 | 52.63 | 63.16 |
|  | MIC | 50 | 6.25 | 6.25 | 6.25 |
| Trichophyton rubrum | IZ | 7 | 11 | 10 | 13 |
|  | % | 31.82 | 50.00 | 45.45 | 59.09 |
|  | MIC | 50 | 6.25 | 6.25 | 6.25 |
| Candida albicans | IZ | 8 | 12 | 11 | 13 |
|  | % | 38.10 | 57.14 | 52.38 | 61.90 |
|  | MIC | 50 | 6.25 | 6.25 | 6.25 |

One potential explanation for this phenomenon is that metal ions have a positive charge which can be neutralized during chelation or the process of forming a complex with a ligand. This electron delocalization across the ring may make the molecule more lipophilic, allowing it to enter the lipid bilayer of the cell membrane. Once inside, the organometallic compound may disrupt binding sites and affect metabolic pathways, leading to the death of the bacteria.

Furthermore, Table 2 compares the inhibition zone values of the identified complexes to those of the antibiotic Chloramphenicol, which has a high activity index and is expected to have a high inhibition zone value. The CuAZD complex demonstrated good antibacterial activity against E. coli, P. aeruginosa, S. aureus, and B. cereus, with activity indexes of 72.22, 65.01, 77.78, and 72.22, respectively. It also showed promising effects against A. flavus, T. rubrum, and C. albicans, with activity indexes of 63.16, 59.09, and 61.90, respectively.

The MIC, or the lowest concentration of a drug that can inhibit the development of bacteria or fungi, is often used as a starting point in larger preclinical studies of new antibacterial medications. The MIC value was obtained by repeatedly diluting a sample until the desired concentration was reached. The MIC values calculated for the drugs under investigation are likewise shown in Table 2, which demonstrates that the metal complexes had a lower MIC (6.25-3.125 ppm) compared to the free ligand (around 50 ppm).

The results indicated that these complexes had comparable biological activity with that in the literature. Thus, these complexes have the potential to act as effective antimicrobials.

Example 4

Molecular Docking

The relationship between the antimicrobial activity of certain complexes and their ability to bind to a specific protein, known as an antimicrobial target protein, was investigated. The molecular docking technique was used to test these complexes, which involves analyzing the 3D structure of the complexes and protein to understand how they fit together. In this case, the complexes, referred to as substrates or ligands, were docked onto a protein [herein is *E. coli* (PDB ID: 5iq9)]. The results of the docking were recorded in Table 3, below.

TABLE 3 molecular docking data

| Ligand | Receptor | Interaction | Distance | E (kcal/mol) | S (kcal/mol) | Ki (μM) |
|---|---|---|---|---|---|---|
| H2AZD | O 19 | PRO 41 | H-donor | 2.96 | −2.30 | −5.55 | 86.51 |
| FeAZD | O 31 | ASP 85 | H-donor | 2.57 | −6.80 | −6.92 | 8.59 |
| | CL 32 | THR 164 | H-donor | 3.01 | −2.10 | | |
| | N 12 | ASP 85 | ionic | 3.14 | −3.60 | | |
| | O 31 | ASP 85 | ionic | 2.57 | −8.10 | | |
| NiAZD | O 31 | ASP 85 | H-donor | 2.70 | −12.50 | −6.63 | 14.01 |
| | N 12 | ASP 85 | ionic | 3.73 | −1.10 | | |
| | O 31 | ASP 85 | ionic | 2.70 | −6.80 | | |
| CuAZD | O 31 | ASP 85 | H-donor | 3.13 | −7.50 | −7.05 | 6.90 |
| | O 32 | ASP 85 | H-donor | 2.76 | −7.80 | | |
| | O 33 | GLY 42 | H-donor | 2.79 | −4.30 | | |
| | O 31 | ASP 85 | ionic | 3.13 | −3.70 | | |
| | O 32 | ASP 85 | ionic | 2.95 | −4.80 | | |
| | 6-ring | LYS 103 | pi-cation | 4.78 | −0.80 | | |

The docking results show strong interactions between the substrates and the protein's active site, including hydrophobic and hydrogen bonding interactions. Among the chemicals tested, CuAZD had the highest inhibitory potential, followed by FeAZD, NiAZD, and H$_2$AZD. CuAZD, the most effective compound, interacted with the protein through hydrogen bonds and hydrophobic interactions, as presented in Table 3.

The inhibition constant, or Ki value, of a compound, can be used to determine its potential as a hit, lead, or therapeutic candidate. A lower Ki value suggests a stronger action and is therefore more favorable. The Ki values for the chemicals in this study ranged from 6.90 for CuAZD to 86.51 for NiAZD. Based on these results, it appears that CuAZD may be a promising therapeutic option due to its low Ki value.

Overall, this study demonstrated that molecular docking can be used to predict the binding affinity of compounds to an antimicrobial target protein and to identify potential therapeutic candidates. Further research will be needed to approve these findings and to evaluate the effectiveness of these chemicals as potential treatments.

The results indicated that these compounds had comparable docking binding activity with that in the literature.

The current compounds form strong interactions with the residual amino acids inside the receptor active site. More specifically, CuAZD forms three H-donor, two ionic, and one pi-cation interactions. CuAZD forms three H-donor between O31-ASP85, O32-ASP85, and O33-GLY42, with distances of 3.13, 2.76, and 2.79 Å. Moreover, CuAZD forms two ionic interactions as O31-ASP85, and O32-ASP85, with distances of 3.13, and 2.95 Å, in addition to one pi-cation between 6-ring-LYS103 with a distance of 4.78 Å. The free ligand forms one H-donor interaction between O19 with PRO41 with a distance of 2.96 Å.

It is to be understood that the metal-H$_2$ADZ complex is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating a microbial infection in a subject, comprising administering to the subject a therapeutically effective amount of a metal-1-(2-hydroxyphenylazo)-2-naphthol complex; wherein the complex is selected from the group consisting of:

FeAZD complex;

NiAZD complex; and

CuAZD complex.

2. The method of claim 1, wherein the microbial infection is a bacterial infection or a fungal infection.

3. The method of claim 2, wherein the bacterial infection or the fungal infection is caused by one or more of *Escherichia coli*, *Pseudomonas aeruginosa*, *Staphylococcus aureus*, *Bacillus cereus*, *Trichophyton rubrum*, *Aspergillus flavus*, and *Candida albicans*.

\* \* \* \* \*